United States Patent
Mochizuki

(10) Patent No.: US 11,850,343 B2
(45) Date of Patent: Dec. 26, 2023

(54) BLOOD PURIFICATION DEVICE AND COUPLER

(71) Applicant: Nikkiso Co., Ltd., Tokyo (JP)

(72) Inventor: Hiroaki Mochizuki, Hakusan (JP)

(73) Assignee: NIKKISO CO., LTD., Tokyo (JP)

( * ) Notice: Subject to any disclaimer, the term of this patent is extended or adjusted under 35 U.S.C. 154(b) by 767 days.

(21) Appl. No.: 16/393,044

(22) Filed: Apr. 24, 2019

(65) Prior Publication Data
US 2019/0247559 A1 Aug. 15, 2019

Related U.S. Application Data

(63) Continuation of application No. PCT/JP2017/037847, filed on Oct. 19, 2017.

(30) Foreign Application Priority Data

Oct. 25, 2016 (JP) .................................. 2016-208979

(51) Int. Cl.
*A61M 1/16* (2006.01)
*A61L 2/26* (2006.01)
(Continued)

(52) U.S. Cl.
CPC .............. *A61M 1/168* (2013.01); *A61L 2/10* (2013.01); *A61L 2/26* (2013.01); *A61M 1/14* (2013.01);
(Continued)

(58) Field of Classification Search
CPC .... A61L 2202/11; A61L 2202/17; A61L 2/10; A61L 2/26; A61L 2/0017; A61L 2/0023;
(Continued)

(56) References Cited

U.S. PATENT DOCUMENTS

| 4,141,686 A | * | 2/1979 | Lewis ....................... A61L 2/10 |
| | | | 250/436 |
| 2004/0262917 A1 | * | 12/2004 | Sunohara ........... A61M 39/1011 |
| | | | 285/277 |

(Continued)

FOREIGN PATENT DOCUMENTS

| CN | 103830756 A | 6/2014 |
| CN | 205126917 U | 4/2016 |

(Continued)

OTHER PUBLICATIONS

Office Action issued in corresponding CN Patent Application No. 201780066137.9 dated Dec. 28, 2020, with English translation (26 pages).

(Continued)

*Primary Examiner* — Bobby Ramdhanie
*Assistant Examiner* — Donovan Bui-Huynh
(74) *Attorney, Agent, or Firm* — Muncy, Geissler, Olds & Lowe

(57) ABSTRACT

A blood purification device includes: a control device that controls supply of a dialysis solution to a blood purifier; a dialysis solution supply tube in which a dialysis solution flows from the control device toward the blood purifier; a dialysis solution discharge tube in which the dialysis solution flows from the blood purifier toward the control device; a supply side coupler that connects between the dialysis solution supply tube and a dialysis solution inflow pipe of the blood purifier; and a discharge side coupler that connects between the dialysis solution discharge tube and a dialysis solution outflow pipe of the blood purifier. At least one of the supply side coupler and the discharge side coupler includes a light source unit configured to irradiate the interior of the coupler with ultraviolet light.

8 Claims, 3 Drawing Sheets

(51) Int. Cl.
*A61L 2/10* (2006.01)
*A61M 39/16* (2006.01)
*A61M 1/14* (2006.01)

(52) U.S. Cl.
CPC .............. *A61M 1/16* (2013.01); *A61M 39/16* (2013.01); *A61L 2202/11* (2013.01); *A61L 2202/17* (2013.01); *A61M 2205/14* (2013.01); *A61M 2205/3334* (2013.01); *A61M 2205/8206* (2013.01); *A61M 2209/10* (2013.01)

(58) Field of Classification Search
CPC .............. A61L 2/0047; A61L 2202/21; A61L 2202/24; A61M 1/14; A61M 1/16; A61M 1/168; A61M 1/1688; A61M 2205/14; A61M 2205/3334; A61M 2205/8206; A61M 2209/08; A61M 2209/10; A61M 39/16; A61M 1/28; A61M 39/1011; A61M 1/1656; A61M 1/1666; A61M 1/1672; A61M 1/1674; A61M 1/1686; A61M 1/282; A61M 1/287; A61M 2039/1027; A61M 2205/50; A61M 2205/502; A61M 2205/75; A61M 2205/7518; A61M 1/1605; A61M 1/285; A61M 2039/167; A61M 2205/12; A61M 2205/18; A61M 2205/3331; A61M 2205/3337; A61M 2205/3368; A61M 2205/3584; A61M 2209/084; A61M 39/18; A61M 39/22; A61K 31/19; A61K 31/7004; A61K 31/716; A61K 33/00; A61K 33/06; A61K 33/14
See application file for complete search history.

(56) References Cited

U.S. PATENT DOCUMENTS

| | | | | |
|---|---|---|---|---|
| 2005/0006297 | A1* | 1/2005 | Moriwaki | A61M 39/1011 210/321.6 |
| 2006/0144776 | A1* | 7/2006 | Mishkin | B01D 61/30 134/186 |
| 2009/0012459 | A1* | 1/2009 | Sobue | A61M 39/18 604/29 |
| 2013/0303996 | A1* | 11/2013 | Rasooly | A61L 2/10 604/264 |
| 2014/0138301 | A1* | 5/2014 | Iwahori | A61M 1/3649 210/321.72 |
| 2017/0281845 | A1* | 10/2017 | Manda | C02F 1/42 |
| 2018/0043081 | A1* | 2/2018 | Lura | A61M 1/1656 |

FOREIGN PATENT DOCUMENTS

| | | |
|---|---|---|
| CN | 106029158 A | 10/2016 |
| JP | 2758148 B2 | 3/1998 |
| JP | 2002-219169 A | 8/2002 |
| JP | 2010-532238 A | 10/2010 |
| JP | 2010-263999 A | 11/2010 |
| JP | 2014-097197 A | 5/2014 |
| JP | 2014097197 A * | 5/2014 |
| WO | WO-2016149645 A1 | 9/2016 |

OTHER PUBLICATIONS

European Search Report cited in counterpart application EP 17864030.6, dated May 7, 2020, 10 pages.
Office Action issued in CN 201780066137.9 dated Aug. 16, 2021 with English translation, 23 pages.
Office Action dated Jan. 19, 2022 in CN Application No. 201780056137.9, 21 pages, w/English-language translation.

* cited by examiner

BLOOD PURIFICATION DEVICE AND COUPLER

RELATED APPLICATION

Priority is claimed to Japanese Patent Application No. 2016-208979, filed on Oct. 25, 2016, the entire content of which is incorporated herein by reference.

BACKGROUND OF THE INVENTION

1. Field of the Invention

The present invention relates to a blood purification device, and, more particularly, to a coupler connected to a joint pipe of a blood purifier.

2. Description of the Related Art

In a blood purification process such as blood dialysis, a blood purifier called a dialyzer is used. A dialysis solution inflow pipe and a dialysis solution outflow pipe are provided in the blood purifier. A tube for supplying a dialysis solution is detachably connected to the dialysis solution inflow pipe via a coupler, and a tube for discharging a dialysis solution is detachably connected to the dialysis solution outflow pipe via a coupler. While the blood purifier is not being used (more specifically, when it is being cleaned or sterilized), the couplers on the supply side and the discharge side are detached from the blood purifier, and the route in which the dialysis solution flows is cleaned or sterilized by connecting the couplers to each other.

The coupler connected to the blood purifier is detached and comes into contact with ambient air when a purification process is started or ended and so might be contaminated when exposed to air. Further, the connection part of the coupler that comes into contact with the dialysis solution inflow pipe or the dialysis solution outflow pipe has a female connector shape so that it might be difficult to clean or sterilize the connection part by wiping it with alcohol, etc.

SUMMARY OF THE INVENTION

In this background, an illustrative purpose of the present invention is to provide a technology of sterilizing the interior of a coupler connected to a blood purifier.

A blood purification device according to one embodiment of the present invention includes: a control device that controls supply of a dialysis solution to a blood purifier; a dialysis solution supply tube in which the dialysis solution flows from the control device toward the blood purifier; a dialysis solution discharge tube in which the dialysis solution flows from the blood purifier toward the control device; a supply side coupler that connects between the dialysis solution supply tube and a dialysis solution inflow pipe of the blood purifier; and a discharge side coupler that connects between the dialysis solution discharge tube and a dialysis solution outflow pipe of the blood purifier. At least one of the supply side coupler and the discharge side coupler includes a light source unit configured to irradiate an interior of the coupler with ultraviolet light.

According to the embodiment, the interior of the coupler connected to the blood purifier is sterilized by irradiating the interior of the coupler with ultraviolet light. This maintains the coupler in a sanitized condition.

The supply side coupler may include a pipe connection part detachably connected to the dialysis solution inflow pipe. The discharge side coupler may include a pipe connection part detachably connected to the dialysis solution outflow pipe. The light source unit may be configured to irradiate the pipe connection part exposed by being detached from the dialysis solution inflow pipe or the dialysis solution outflow pipe with ultraviolet light.

The control device may be configured to perform a cleaning process of circulating a cleaning solution in a route passing through the dialysis solution supply tube, the supply side coupler, the discharge side coupler, and the dialysis solution discharge tube while the supply side coupler detached from the dialysis solution inflow pipe and the discharge side coupler detached from the dialysis solution outflow pipe are connected to each other. The light source unit may radiate ultraviolet light while the cleaning process is being performed.

The control device may include a coupler holder configured to temporarily hold the supply side coupler detached from the dialysis solution inflow pipe and the discharge side coupler detached from the dialysis solution outflow pipe. The light source unit may include a power reception unit configured to receive power from the control device while the supply side coupler and the discharge side coupler are being held by the coupler holder.

The power reception unit may be configured to receive power from the control device in a contactless scheme.

The light source unit may be configured not to be lighted when the light source unit is detached from the coupler holder.

The light source unit may irradiate the dialysis solution flowing inside the coupler with ultraviolet light while a dialytic process of supplying the dialysis solution to the blood purifier is being performed.

The light source unit may be configured to be detachable from a main part of the supply side coupler or the discharge side coupler.

A main part of at least one of the supply side coupler and the discharge side coupler may be provided with a window member that transmits ultraviolet light from the light source unit.

At least one of the supply side coupler and the discharge side coupler may include a main part, a pipe connection part adjacent to the main part in an axial direction, and a tube connection part extending from the main part in a direction perpendicular to the axial direction so as to form an L shape. The light source unit may be configured to radiate ultraviolet light in the axial direction from the main part toward the pipe connection part.

Another embodiment of the present invention relates to a coupler. The coupler is for connecting between a dialysis solution tube for supplying or discharging a dialysis solution and a joint pipe of a blood purifier, comprising a light source unit configured to irradiate an interior of the coupler with ultraviolet light.

According to the embodiment, the interior of the coupler connected to the blood purifier is sterilized by irradiating the interior of the coupler with ultraviolet light. This maintains the coupler in a sanitized condition.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

The invention will now be described by reference to the preferred embodiments. This does not intend to limit the scope of the present invention, but to exemplify the invention.

A detailed description will be given of embodiments to practice the present invention with reference to the drawings. Like numerals are used in the description to denote like elements and a duplicate description is omitted as appropriate.

Figure 1:
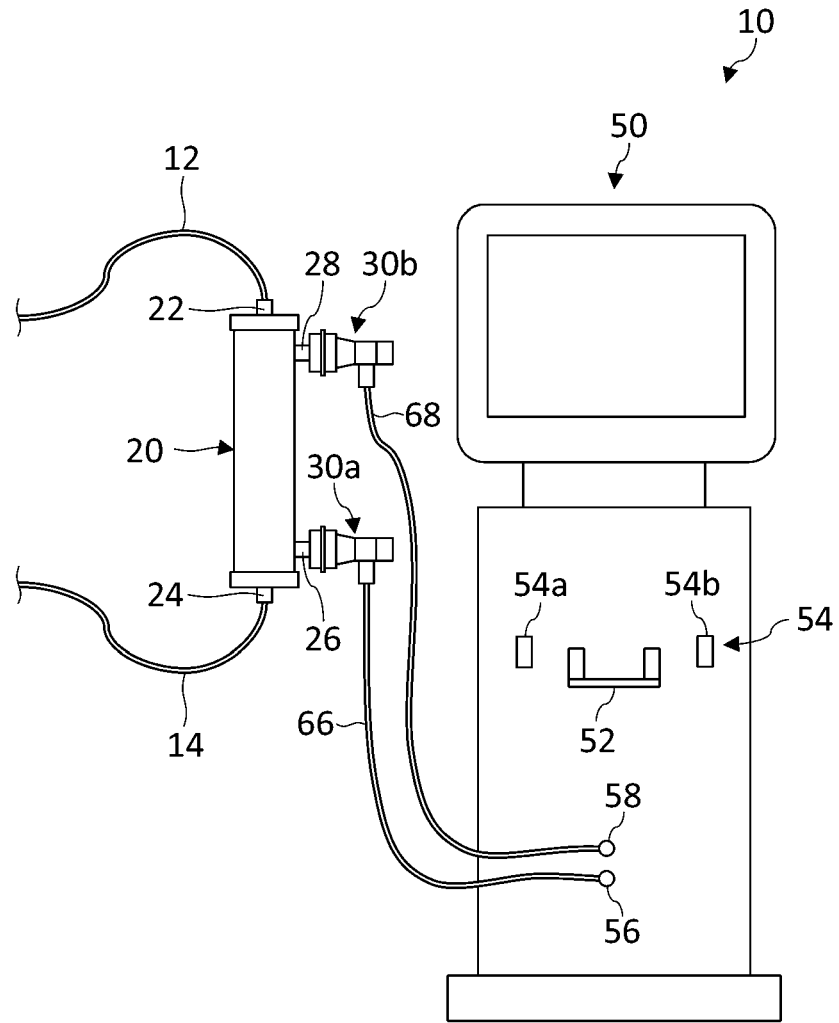
FIG. 1 schematically shows a configuration of a blood purification device according to the embodiment.

FIG. 1 schematically shows a configuration of a blood purification device 10 according to the embodiment. The blood purification device 10 includes a supply side coupler 30a, a discharge side coupler 30b, a control device 50, a dialysis solution supply tube 66, a dialysis solution discharge tube 68. The blood purification device 10 is a system for performing a blood purification process such as blood dialysis and purifies the blood circulating inside a body by using a blood purifier 20 called a dialyzer. The blood purification device 10 is detachably connected to the blood purifier 20 via the supply side coupler 30a and the discharge side coupler 30b.

The blood purifier 20 includes a blood inflow port 22, a blood outflow port 24, a dialysis solution inflow pipe 26, and a dialysis solution outflow pipe 28. The blood inflow port 22 is connected to an arterial blood circuit 12, and the blood outflow port 24 is connected to an intravenous blood circuit 14. The dialysis solution inflow pipe 26 is connected to the dialysis solution supply tube 66 via the supply side coupler 30a, and the dialysis solution supplied from the control device 50 flows into the dialysis solution inflow pipe 26. The dialysis solution outflow pipe 28 is connected to the dialysis solution discharge tube 68 via the discharge side coupler 30b, and the dialysis solution discharged toward the control device 50 flows out of the dialysis solution outflow pipe 28.

The blood purifier 20 contains hollow fibers inside, and the interior of the hollow fibers serves as a flow passage of the blood connecting the blood inflow port 22 and the blood outflow port 24. Meanwhile, the exterior of the hollow fibers serves as a flow passage for the dialysis solution connecting the dialysis solution inflow pipe 26 and the dialysis solution outflow pipe 28. A large number of bores are formed in the hollow fibers, and the hollow fibers are configured to permeate the waste matter, excess moisture, etc. in the blood via the large number of bores. An unused blood purifier 20 is used for each session of dialytic treatment of a patient and is exchanged at each dialytic process.

The supply side coupler 30a connects between the dialysis solution inflow pipe 26 and the dialysis solution supply tube 66. The discharge side coupler 30b connects between the dialysis solution outflow pipe 28 and the dialysis solution discharge tube 68. The supply side coupler 30a and the discharge side coupler 30b are so-called one-touch couplers and have a female connector structure. The supply side coupler 30a is detachably connected to the dialysis solution inflow pipe 26 by, for example, manipulating a slide member provided on the outer circumference of the supply side coupler 30a. Similarly, the discharge side coupler 30b is detachably connected to the dialysis solution outflow pipe 28 by, for example, manipulating a slide member provided on the outer circumference of the discharge side coupler 30b.

Figure 2:
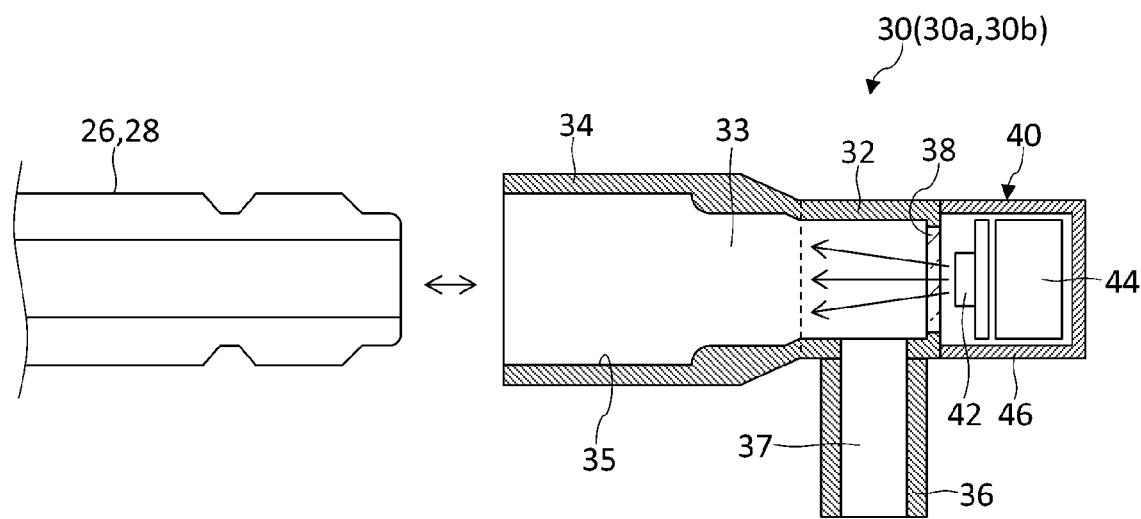
FIG. 2 is a cross-sectional view schematically showing a configuration of the coupler.

FIG. 2 is a cross-sectional view schematically showing a configuration of the coupler 30 (the supply side coupler 30a or the discharge side coupler 30b). In this embodiment, the supply side coupler 30a and the discharge side coupler 30b have a similar structure so that these may be generically referred to as the "coupler 30".

The coupler 30 includes a main part 32, a pipe connection part 34, a tube connection part 36, a window member 38, and a light source unit 40. The coupler 30 is configured such that the main part 32, the pipe connection part 34, and the tube connection part 36 form an L shape. The pipe connection part 34 is adjacent to the main part 32 in the axial direction and form a first flow passage 33 extending in the axial direction along with the main part 32. The tube connection part 36 extends from the main part 32 in a direction perpendicular to or intersecting the axial direction. The tube connection part 36 forms a second flow passage 37 extending to form an L shape as a bent extension from the first flow passage 33 extending in the axial direction.

The pipe connection part 34 is a part detachably connected to the dialysis solution inflow pipe 26 or the dialysis solution outflow pipe 28, which are joint pipes of the blood purifier 20. The pipe connection part 34 has a female connector structure. An inner surface 35 of the pipe connection part 34 and the outer circumference of the joint pipe (the dialysis solution inflow pipe 26 or the dialysis solution outflow pipe 28) are in contact or engaged with each other to establish connection. The tube connection part 36 is a part connected to an end of the dialysis solution supply tube 66 or the dialysis solution discharge tube 68. By being inserted into an end of the dialysis solution supply tube 66 or the dialysis solution discharge tube 68, the tube connection part 36 is connected to the tube.

The window member 38 is provided in the main part 32 and is arranged to transmit ultraviolet light from the light source unit 40 in the axial direction. The window member 38 is preferably made of a material having a high ultraviolet transmittance and is made of quartz ($SiO_2$), sapphire ($Al_2O_3$), amorphous fluororesin, or the like.

The light source unit 40 is provided adjacent to the window member 38 and is fixed to the main part 32. The light source unit 40 is attached to the main part 32 detachably or in a manner that it is easily detached. The light source unit 40 includes a light emitting device 42, a power reception unit 44, and a housing 46. The light emitting device 42 and the power reception unit 44 are housed inside the housing 46.

The light emitting devices 42 is a so-called ultra violet-light emitting diode (UV-LED) and outputs ultraviolet light having a central wavelength or a peak wavelength included in a range of about 200 nm~350 nm. It is preferred that the light emitting device 42 emit ultraviolet light near 260 nm~290 nm having a high sterilizing efficiency. Such a deep ultraviolet LED is exemplified by an aluminum gallium nitride (AlGaN) based LED.

The power reception unit 44 is configured to receive power supplied from outside the light source unit 40. The power reception unit 44 is configured to receiver power in a so-called contactless scheme. For example, the power reception unit 44 includes a coil 48 (48a, 48b), etc. for receiving power transmitted by using electromagnetic waves. The power reception unit 44 may be configured to receive power in a contact scheme and may include a metal terminal for receiving power. The power reception unit 44 is configured to supply power to the light emitting device 42. For example, the power reception unit 44 includes a circuit to drive the light source unit 40. The power reception unit 44 may not include a circuit to drive the light source unit 40, and the received power may be directly supplied to the light source unit 40. The power reception unit 44 may include a power storage unit for temporarily storing the power that should be supplied to the light emitting device 42. The power storage unit included in the power reception unit 44 may be comprised of a secondary battery that can be charged and discharged.

The light source unit 40 is configured to irradiate the interior of the main part 32 and the pipe connection part 34 of the coupler 30 with ultraviolet light. The light source unit 40 radiates ultraviolet light in the axial direction along the first flow passage 33 to irradiate the inner side of the main part 32 and the pipe connection part 34 with ultraviolet light. In particular, the light source unit 40 irradiates the inner surface 35 of the pipe connection part 34 configured to come into contact with the the dialysis solution inflow pipe 26 or the dialysis solution outflow pipe 28 so that the inner surface 35 is sterilized or disinfected.

The coupler 30 is made of, for example, a resin material. It is preferred that the coupler 30 be made of a material having a high durability against deep ultraviolet light. For example, the coupler 30 is made of a fluororesin such as polytetrafluoroethylene (PTFE). At least the inner surface 35 of the coupler 30 may be made of a material having a high ultraviolet reflectivity (e.g., PTFE). By configuring at least the inner surface 35 of the coupler 30 to be made of a material having a high ultraviolet reflectivity, it is possible to propagate the ultraviolet light in the axial direction, reflecting the ultraviolet light on the inner surface 35.

Referring back to FIG. 1, the control device 50 is configured to control the supply of the dialysis solution to and the discharge of the dialysis solution from the blood purifier 20. The control device 50 includes a dialysis solution supply port 56 connected to the dialysis solution supply tube 66 and a dialysis solution discharge port 58 connected to the dialysis solution discharge tube 68. The control device 50 includes a pump (not shown) for supplying and discharging the dialysis solution and controls the flow of the dialysis solution to the blood purifier 20 by controlling the operation of the pump.

Figure 3:
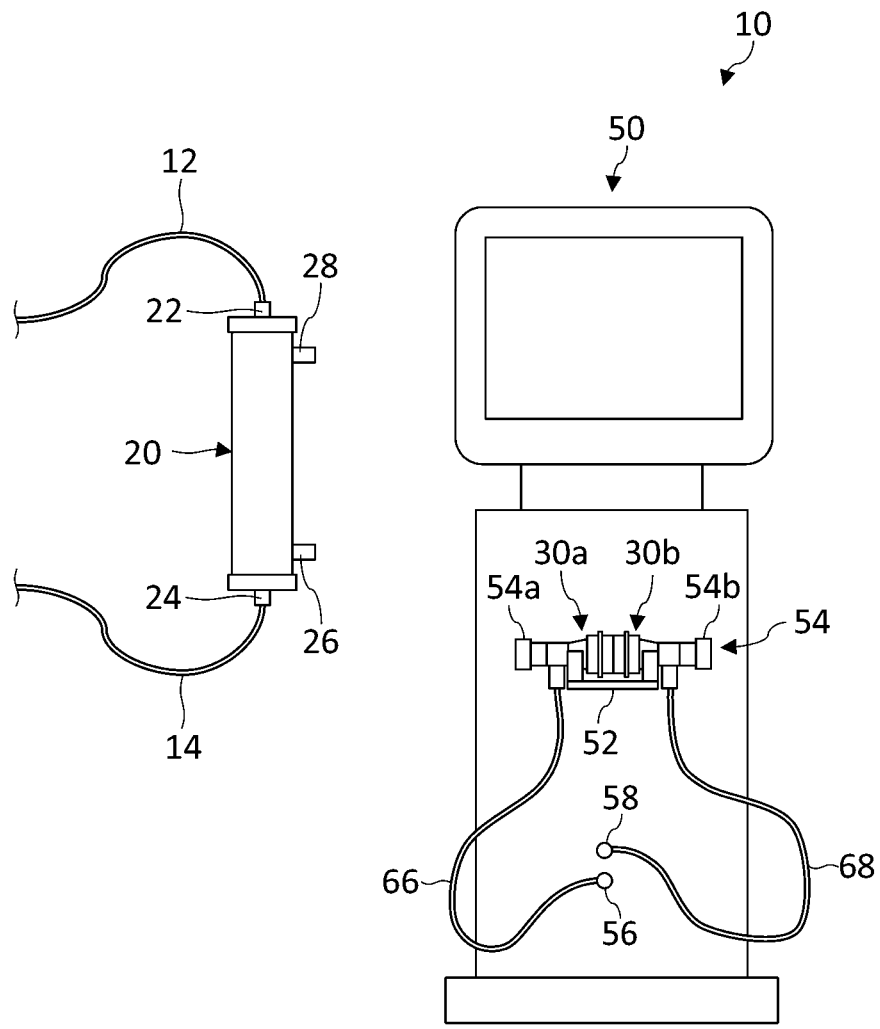
FIG. 3 schematically shows how the couplers are held by the coupler holder.

The control device 50 includes a coupler holder 52. The coupler holder 52 is provided to hold the supply side coupler 30a and the discharge side coupler 30b temporarily while the blood purifier 20 is not being used. FIG. 3 schematically shows how the couplers 30a, 30b are held by the coupler holder 52. While the blood purifier 20 is not being used, the supply side coupler 30a and the discharge side coupler 30b are detached from the blood purifier 20 and the openings thereof are connected to each other. While the supply side coupler 30a and the discharge side coupler 30b are connected, the coupler holder 52 temporarily holds or engages both of the couplers 30a, 30b.

The supply side coupler 30a and the discharge side coupler 30b may be connected to each other via a dedicated adaptor or connector. Alternatively, the supply side coupler 30a and the discharge side coupler 30b may be configured such that they can be directly connected. By connecting the supply side coupler 30a and the discharge side coupler 30b to each other, a continuous circulation route passing through the dialysis solution supply port 56, the dialysis solution supply tube 66, the supply side coupler 30a, the discharge side coupler 30b, the dialysis solution discharge tube 68, and the dialysis solution discharge port 58 is built. A cleaning solution for cleaning the interior of the tubes and the couplers forming the route is circulated in the circulation route. The control device 50 performs a cleaning process of circulating the cleaning solution while the supply side coupler 30a and the discharge side coupler 30b are connected. The cleaning solution circulated for cleaning is not limited to a particular type. Water (e.g., pure water), an antiseptic solution such as an aqueous solution of sodium hypochlorite and an acetyl hydroperoxide solution, or a dialysis solution can be used as the cleaning solution.

The control device 50 includes a power feeding unit 54. The power feeding unit 54 feeds power to the power reception unit 44 of the couplers 30a, 30b held by the coupler holder 52. The power feeding unit 54 includes a first power feeding unit 54a for supplying power to one of the couplers 30a, 30b and a second power feeding unit 54b for supplying power to the other of the couplers 30a, 30b. The first power feeding unit 54a and the second power feeding unit 54b are provided in the neighborhood of the light source unit 40 (the power reception unit 44) of the couplers 30a, 30b held by the coupler holder 52. The power feeding unit 54 includes a coil 60a, 60b, etc. for supplying power in a contactless scheme. The power feeding unit 54 may include a power feeding terminal for supplying power in a contact scheme.

Figure 4:
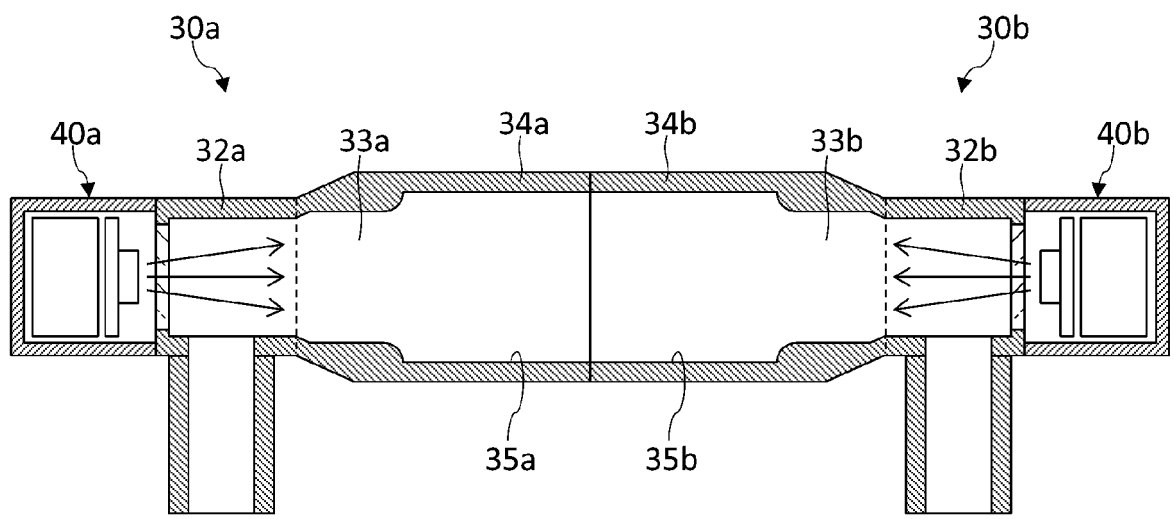
FIG. 4 is a cross-sectional view schematically showing the couplers that are being cleaned.

FIG. 4 is a cross-sectional view schematically showing the couplers 30a, 30b that are being cleaned. As shown in the figure, the openings of the pipe connection parts 34a, 34b of the couplers 30a, 30b are connected to each other, and the first flow passages 33a, 33b of the couplers form a single flow passage extending in the axial direction. The light source units 40a, 40b face each other in the axial direction, sandwiching the first flow passages 33a, 33b and emit ultraviolet light in the axial direction. This causes the interior of the main parts 32a, 32b of the couplers and the inner surfaces 35a, 35b of the pipe connection parts 34a, 34b of the couplers to be sterilized by ultraviolet irradiation.

The light source units 40 (40a, 40b) may be configured to radiate ultraviolet light only while the couplers are held by the coupler holder 52. For example, the light source units 40 may be configured to be lighted only while power is being fed from the power feeding unit 54. In other words, the light source units 40 may be configured not to be lighted while power is not being fed from the power feeding unit 54 and configured not to be lighted when the light source units 40 are detached from the coupler holder 52. This prevents the ultraviolet light from the light source units 40 from leaking outside when the coupler 30 is attached to the blood purifier 20.

According to the configuration described above, the interior of the couplers 30a, 30b, detached from the blood purifier 20 when a dialytic process is not performed, can be sterilized with ultraviolet light by connecting the couplers 30a, 30b and placing the couplers 30a, 30b in the coupler holder 52. This allows the interior of the couplers 30a, 30b, which are repeatedly used in multiple dialytic processes, can be maintained in a sanitized condition. Since the sterilization process is automatically started merely by setting the couplers 30a, 30b in the coupler holder 52, the healthcare professional using the blood purification device 10 can sterilized the couplers without any additional work.

According to the embodiment, power is fed to the light source unit 40 of the coupler 30 in a contactless scheme so that it is not necessary to expose a metallic component such as a power supply terminal to the light source unit 40. The coupler 30 comes into contact with the dialysis solution. If a metallic component is exposed, therefore, it may become rusty easily and present a sanitary problem. According to the embodiment, power is fed in a contactless scheme so that it is easy to maintain the coupler 30 in a sanitized condition. By setting the coupler in the coupler holder 52 to feed power, it is no longer necessary to provide a power cable etc. for feeding power to the light source unit 40 separately, and the coupler 30 can be detached without caring about the routing of the cable.

According to the embodiment, the light source unit 40 is configured to be detachable from the main part 32 of the coupler 30 so that the maintainability of the coupler 30 is improved. For example, when a trouble occurs in the light source unit 40, only the light source unit 40 may be replaced. Further, only the connector structure of the coupler 30, including the main part 32, may be replaced, and the previous light source unit 40 may be attached to the new main part 32. This decreases the cost incurred for maintenance as compared with the case of replacing the entirety of the coupler 30.

Described above is an explanation based on an exemplary embodiment. The embodiment is intended to be illustrative only and it will be understood by those skilled in the art that various design changes are possible and various modifications are possible and that such modifications are also within the scope of the present invention.

In the embodiment described above, the light source unit 40 is provided in both the supply side coupler 30a and the discharge side coupler 30b. In a variation, the light source unit 40 is provided only in one of the supply side coupler 30a and the discharge side coupler 30b, and the light source unit 40 may not be provided in the other.

Figure 5:
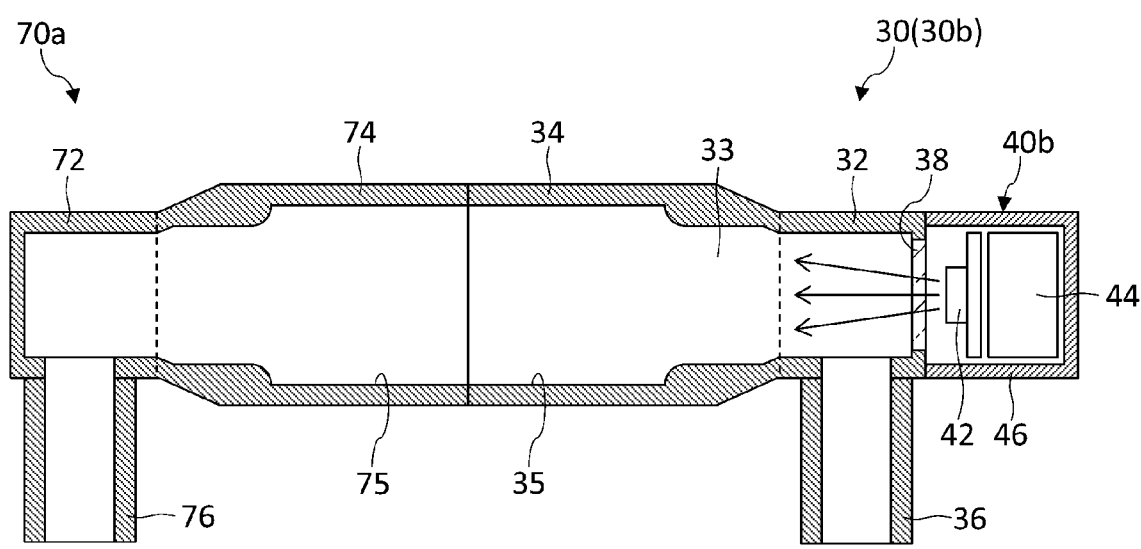
FIG. 5 is a cross-sectional view schematically showing couplers according to a variation.

FIG. 5 is a cross-sectional view schematically showing couplers 70a, 30b according to a variation. In this variation, the supply side coupler 70a that does not include the light source unit 40 is used in place of the supply side coupler 30a. The supply side coupler 70a includes a main part 72, a pipe connection part 74, and a tube connection part 76. As shown in the figure, the supply side coupler 70a is connected to the discharge side coupler 30b during a cleaning process. The interior of the main part 72 and an inner surface 75 of the pipe connection part 74 of the supply side coupler 70a are sterilized by ultraviolet irradiation from the light source unit 40b of the discharge side coupler 30b. Thus, the variation also allows the interior of the couplers 70a, 30b to be sterilized by ultraviolet light. In a further variation, the light source unit 40 may be provided in the supply side coupler 30a, and the light source unit 40 may not be provided in the discharge side coupler.

In the embodiment described above, the light source unit 40 is described as radiating ultraviolet during a cleaning process. In a further variation, the light source unit 40 may radiate ultraviolet light while a dialytic process is being performed. By irradiating the dialysis solution flowing inside the coupler 30 with ultraviolet light while a dialytic process is being performed, the dialytic solution is sterilized. The light source unit 40 may be lighted by using power collected in the power reception unit 44 or may be lighted by using power supplied via a power supply cable connected to the light source unit 40. When a power supply cable is connected to the light source unit 40, the power supply cable may be provided in the dialysis solution supply tube 66 or the dialysis solution discharge tube 68. For example, the power supply cable may be formed to be integrated with the dialysis solution supply tube 66 or the dialysis solution discharge tube 68.

In the embodiment and variations described above, the coupler 30 is described as having an L shape. In a further variation, the coupler on the dialysis solution side may have a straight shape. In this case, a window member may be provided in a portion of the outer circumference of the coupler, and the light source unit may be attached to outer circumference of the coupler so as to irradiate the interior of the coupler with ultraviolet light.

It should be understood that the invention is not limited to the above-described embodiment but may be modified into various forms on the basis of the spirit of the invention. Additionally, the modifications are included in the scope of the invention.

What is claimed is:

1. A device for controlling and supplying a dialysis solution to a blood purifier, comprising:
   a control device that controls supply of the dialysis solution to the blood purifier;
   a dialysis solution supply tube in which the dialysis solution flows from the control device toward the blood purifier;
   a dialysis solution discharge tube in which the dialysis solution flows from the blood purifier toward the control device;
   a supply side coupler that connects between the dialysis solution supply tube and a dialysis solution inflow pipe of the blood purifier; and
   a discharge side coupler that connects between the dialysis solution discharge tube and a dialysis solution outflow pipe of the blood purifier,
   wherein the control device comprises:
   a coupler holder configured to temporarily hold the supply side coupler detached from the dialysis solution inflow pipe and the discharge side coupler detached from the dialysis solution outflow pipe; and
   a power feeding unit for supplying power;
   wherein at least one of the supply side coupler and the discharge side coupler comprises:
   a light source unit configured to irradiate an interior of the coupler with ultraviolet light; and
   a power reception unit configured to receive power from the power feeding unit in a contactless scheme or in a contact scheme while the supply side coupler and the discharge side coupler are being held by the coupler holder,
   wherein the power reception unit is configured not to receive power from the power feeding unit while the supply side coupler and the discharge side coupler are detached from the coupler holder,
   wherein the light source unit is lighted by using power fed from the power feeding unit when the supply side coupler and the discharge side coupler are being held by the coupler holder and is not lighted when the supply side coupler and the discharge side coupler are detached from the coupler holder, and
   wherein a distance between the power feeding unit and the light source unit is configured to change when the supply side coupler and the discharge side coupler are disconnected from the blood purifier and held on the coupler holder, and are disconnected from the couple holder and connected to the blood purifier.

2. The device according to claim 1, wherein
   the control device includes a power feeding terminal provided in the coupler holder, and the power reception unit includes a power receiving terminal configured to come into contact with the power feeding terminal to establish connection.

3. The device according to claim 1, wherein
the supply side coupler includes a pipe connection part detachably connected to the dialysis solution inflow pipe,
the discharge side coupler includes a pipe connection part detachably connected to the dialysis solution outflow pipe, and
the light source unit is configured to irradiate the pipe connection part exposed by being detached from the dialysis solution inflow pipe or the dialysis solution outflow pipe with ultraviolet light.

4. The device according to claim 1, wherein
the control device is configured to perform a cleaning process of circulating a cleaning solution in a route passing through the dialysis solution supply tube, the supply side coupler, the discharge side coupler, and the dialysis solution discharge tube while the supply side coupler detached from the dialysis solution inflow pipe and the discharge side coupler detached from the dialysis solution outflow pipe are connected to each other, and
the light source unit radiates ultraviolet light while the cleaning process is being performed.

5. The device according to claim 1, wherein
the light source unit is configured to be detachable from a main part of the supply side coupler or the discharge side coupler.

6. The device according to claim 1, wherein
a main part of at least one of the supply side coupler and the discharge side coupler is provided with a window member that transmits ultraviolet light from the light source unit.

7. The device according to claim 1, wherein
at least one of the supply side coupler and the discharge side coupler includes a main part, a pipe connection part adjacent to the main part in an axial direction, and a tube connection part extending from the main part in a direction perpendicular to the axial direction so as to form an L shape, and
the light source unit is configured to radiate ultraviolet light in the axial direction from the main part toward the pipe connection part.

8. The device according to claim 1, wherein
the power feeding unit comprises a coil for supplying power,
the power reception unit comprises a coil for receiving power from the coil of the power feeding unit.

* * * * *